: US 8,116,599 B2
: Feb. 14, 2012

(12) United States Patent
Iwakiri et al.

(54) RADIATION IMAGE SIGNAL OUTPUT CONTROL METHOD AND APPARATUS

(75) Inventors: Naoto Iwakiri, Kanagawa-ken (JP); Tetsuya Usui, Kanagawa-ken (JP); Takashi Shoji, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 1420 days.

(21) Appl. No.: 11/447,042

(22) Filed: Jun. 6, 2006

(65) Prior Publication Data
US 2006/0280337 A1    Dec. 14, 2006

(30) Foreign Application Priority Data
Jun. 6, 2005    (JP) .................. 2005-165431

(51) Int. Cl.
*G06K 9/22*    (2006.01)
(52) U.S. Cl. ...................................... 382/313
(58) Field of Classification Search .............. None
See application file for complete search history.

(56) References Cited

U.S. PATENT DOCUMENTS

| 7,343,159 | B2 | 3/2008 | Saito et al. | |
| 2005/0148334 | A1* | 7/2005 | Peeters ................ | 455/436 |

FOREIGN PATENT DOCUMENTS

| JP | 7-140255 A | 6/1995 |
| JP | 9170364 A | 6/1997 |
| JP | 2000308126 A | 11/2000 |
| JP | 2003044443 A | 2/2003 |
| JP | 2003-152621 A | 5/2003 |
| JP | 2003250184 A | 9/2003 |
| JP | 2004-152067 A | 5/2004 |
| JP | 2004152067 A | 5/2004 |
| JP | 2004289815 A | 10/2004 |
| JP | 2004297420 A | 10/2004 |
| JP | 2005-013310 A | 1/2005 |
| JP | 2005013310 A | 1/2005 |
| JP | 2005020350 A | 1/2005 |

OTHER PUBLICATIONS

Japanese Office Action corresponding to Japanese Patent Application No. 2005-165431, dated Jun. 22, 2010.
Japanese Office Action dated Oct. 26, 2010, with Partial Translation for Jpa 2005-165431.
Japanese Office Action for JPA 2005-165431; Jun. 21, 2011.

* cited by examiner

*Primary Examiner* — Daniel Mariam
*Assistant Examiner* — Elisa Rice
(74) *Attorney, Agent, or Firm* — Sughrue Mion, PLLC

(57) ABSTRACT

A radiation image signal output control method in which distance information that indicates a distance between a radiation image detection cassette and a receiving unit is obtained by a distance information obtaining means, and wireless signals are controlled by an output control means to be outputted from the radiation image detection cassette if the distance indicated by the distance information obtained by the distance information obtaining means is less than or equal to a predetermined value, and not to be outputted therefrom if the distance is greater than the predetermined value.

9 Claims, 3 Drawing Sheets

RADIATION IMAGE SIGNAL OUTPUT CONTROL METHOD AND APPARATUS

BACKGROUND OF THE INVENTION

1. Field of the Invention

The present invention relates to a radiation image signal output control method and apparatus for controlling output of wireless communication signals from an output unit that reads out image signals from a radiation image recording medium according to a radiation image stored therein and outputs the image signals after converting to wireless communication signals.

2. Description of the Related Art

Various radiation image recording media constructed to receive radiation representing a radiation image to record the radiation image therein are proposed and put into practical use in the medical and other industrial fields.

Such radiation image recording media include, for example, a radiation image detector formed of a semiconductor material that generates electric charges when irradiated with radiation, and such radiation image detectors proposed include so-called "optical readout type" and "TFT readout type" radiation image detectors.

One of the optical readout type radiation image detectors proposed, for example, is constituted by a layer structure that includes the following layers in the order listed below: a first electrode layer that transmits radiation; a recording photoconductive layer that generates electric charges when irradiated with radiation; a charge transport layer that acts as an insulator against the latent image charges and as a conductor for the electric charges of opposite polarity to the latent image charges; a readout photoconductive layer that generates electric charges when irradiated with readout light; and a second electrode layer that includes line electrodes that transmit readout light disposed in parallel with each other. In the radiation image detector described above, radiation representing a radiation image is irradiated on the detector from the side of the first electrode layer, and the radiation image is recorded in the detector by storing electric charges generated in the recording photoconductive layer in accordance with the radiation irradiated thereon in the interface between the recording photoconductive layer and charge transport layer. Thereafter, the detector is scanned with linear readout light in the longitudinal direction of the line electrodes to generate electric charges in the readout photoconductive layer. The electric charges generated in the readout photoconductive layer combine with the electric charges stored in the interface described above and flow out to the line electrodes, which are integrated by a current detection amplifier connected to each of the line electrodes, thereby image signals are obtained from the detector, i.e., the radiation image is read out from the detector.

Further, another type of radiation image recording medium that uses a storage phosphor sheet is also proposed. The storage phosphor sheet is provided on a support medium and a radiation image is stored and recorded thereon by the irradiation of radiation transmitted through a subject. The radiation image recorded on the storage phosphor sheet is read out as image signals by photoelectrically converting stimulated luminescence generated by the irradiation of excitation light on the sheet, such as a laser beam or the like.

Further, a portable cassette constituted by one of the radiation image recording media described above, a readout unit, and the like accommodated in a case is also proposed, which allows recording and reading out of a radiation image at any place, as well as at a predetermined place. Further, a method, in which image signals are outputted from such a portable cassette as wireless communication signals, which are received by a receiving unit such as a computer or the like to display the radiation image on a display as a visible image based on the received wireless communication signals is also proposed as described, for example, in Japanese Unexamined Patent Publication No. 7(1995)-140255.

However, when the image signals are outputted as wireless communication signals in the manner as described above, it is likely, for example, that the wireless communication signals are intercepted by a third individual who is totally unrelated to the hospital where such wireless communication is conducted. This may lead to leakage of the personal information of a patient.

The present invention has been developed in view of the circumstances described above, and it is an object of the present invention to provide a radiation image signal output control method and apparatus which, when radiation signals are outputted as wireless communication signals in the manner as described above, is capable of preventing random interceptions of the wireless communication signals.

SUMMARY OF THE INVENTION

A radiation image signal output control method of the present invention comprises the steps of:

obtaining distance information that indicates a distance between an output unit, which reads out image signals from a radiation image recording medium according to a radiation image recorded thereon and outputs the image signals read out therefrom after converting to wireless communication signals, and a receiving unit that receives the wireless communication signals outputted from the output unit; and controlling the wireless communication signals to be outputted from the output unit if the distance indicated by the distance information obtained is less than or equal to a predetermined value, and not to be outputted therefrom if the distance is greater than the predetermined value.

A radiation image signal output control apparatus of the present invention comprises:

a distance information obtaining means for obtaining distance information that indicates a distance between an output unit, which reads out image signals from a radiation image recording medium according to a radiation image recorded thereon and outputs the image signals read out therefrom after converting to wireless communication signals, and a receiving unit that receives the wireless communication signals outputted from the output unit; and an output control means for controlling the wireless communication signals to be outputted from the control unit if the distance indicated by the distance information obtained by the distance information obtaining means is less than or equal to a predetermined value, and not to be outputted therefrom if the distance is greater than the predetermined value.

In the radiation image signal output control apparatus described above, a configuration may be adopted in which the apparatus further includes an identification means for receiving an identification signal that identifies the receiving unit, and authorizing output of the wireless communication signals from the output unit according to the contents of the identification signal; and the output control means controls the wireless communication signals to be outputted from the output unit if the distance indicated by the distance information obtained by the distance information obtaining means is less than or equal to a predetermined value, and the output of the wireless signals is authorized by the authorization means.

Further, a configuration may be adopted in which the apparatus further includes an exception handling acceptance means for accepting an exception handling signal; and the output control means controls the wireless communication signals to be outputted from the output unit regardless of the distance between the apparatus and the receiving unit when the exception handling signal is accepted by the exception handling acceptance means.

Still further, a configuration may be adopted in which the apparatus further includes a storage means for temporarily storing image signals read out from the radiation image recording medium according to the radiation image recorded thereon; a determination means for determining if the image signals, which are temporarily stored in the storage means and outputted from the output unit after converted to wireless communication signals, are correctly received by the receiving unit; and an image signal control means for making, when the wireless communication signals are determined by the determination means to have been correctly received by the receiving unit, the image signals temporarily stored in the storage means corresponding to the wireless communication signals correctly received by the receiving means unreadable.

According to the radiation image signal output control method and apparatus, distance information that indicates a distance between an output unit, which outputs image signals according to a radiation image after converting to wireless communication signals, and a receiving unit that receives the wireless communication signals outputted from the output unit, and the wireless communication signals is controlled to be outputted from the output unit if the distance indicated by the obtained distance information is less than or equal to a predetermined value, and not to be outputted if the distance is greater than the predetermined value. This may prevent the wireless communication signals from being randomly intercepted, and allows the wireless communication signals to be outputted to particular receiving units, for example, only to those provided in some of the examination rooms or in the hospital, whereby the security for preventing personal information leakage of a patient may be enhanced.

Further, in the radiation image signal output control apparatus, if a configuration is adopted in which an identification signal that identifies a receiving unit is accepted to authorize the output of the wireless communication signals from the output unit according to the contents of the identification signal, and the output of the wireless signals from the output unit is allowed when the distance described above is less than or equal to a predetermined value and the output of the wireless communication signals is authorized, the security for preventing a personal information leakage of a patient may be further enhanced.

Still further, if a configuration is adopted in which an exception handling signal is available, and the wireless communication signals are outputted from the output unit regardless of the distance described above when the exception handling signal is accepted, the wireless signals may be outputted appropriately when, for example, an output request for the wireless communication signals is received from a remote place because of an emergency state.

Further, in the case where image signals read out from a radiation image recording medium are temporarily stored in the storage means, if a configuration is adopted in which determination is made if the image signals, which are temporarily stored in the storage means and outputted from the output unit after converted to wireless communication signals, have been correctly received by the receiving unit, and if determined to have been correctly received, the image signals temporarily stored in the storage means is made unreadable, unauthorized reading out of the image signals temporarily stored in the storage means may be prevented.

DESCRIPTION OF THE PREFERRED EMBODIMENTS

Figure 1:
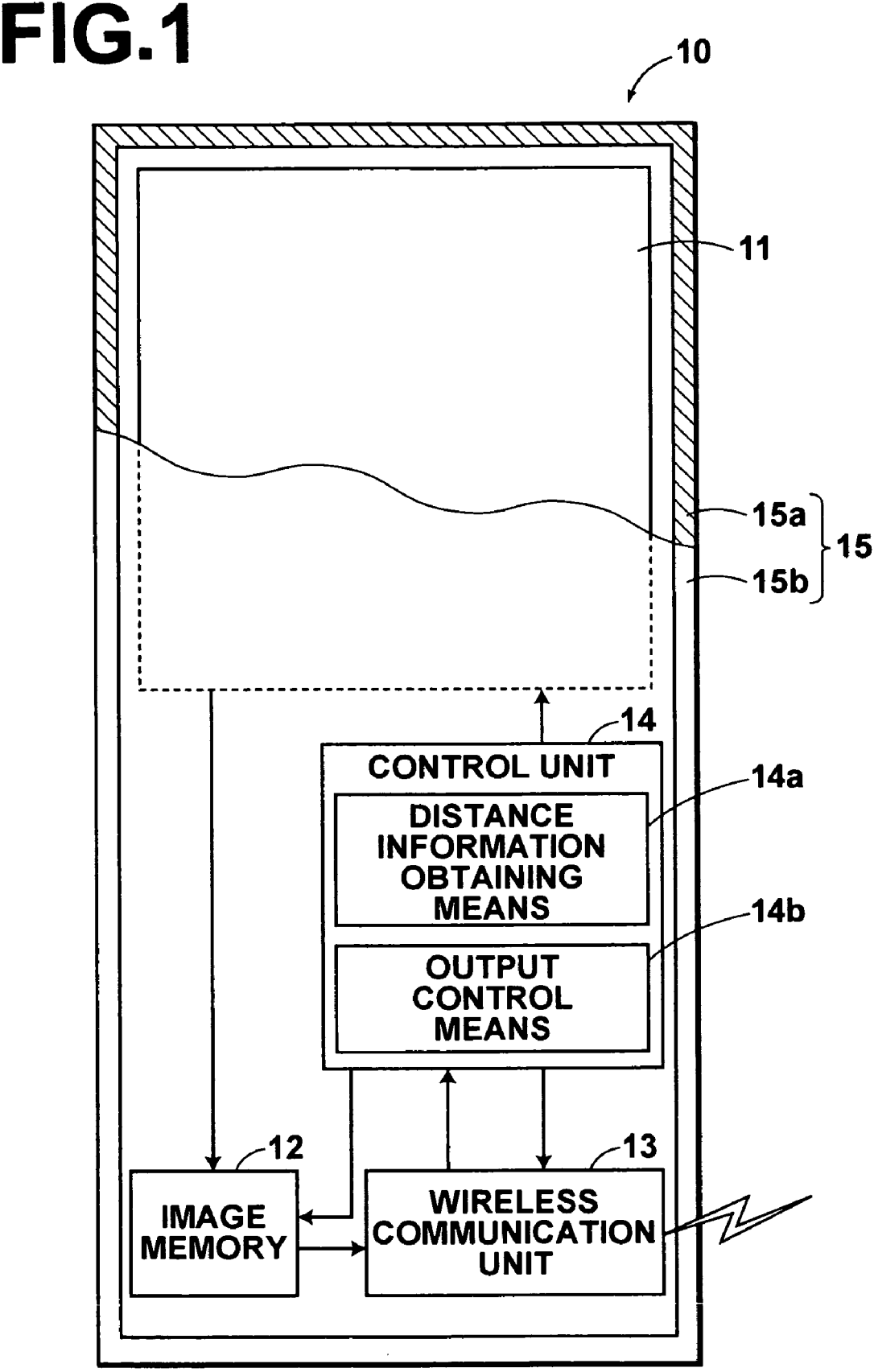
FIG. 1 is a schematic view of a radiation image detection cassette that uses the radiation image signal output control apparatus according to an embodiment of the present invention, illustrating the schematic construction thereof.

Hereinafter, embodiments of the radiation image signal output control method and apparatus of the present invention will be described with reference to accompanying drawings. FIG. 1 is a schematic view of a radiation image detection cassette that uses the radiation image signal output control apparatus according to an embodiment of the present invention, illustrating the schematic construction thereof.

As shown in FIG. 1, the present radiation image detection cassette 10 includes a radiation image detector 11 which is capable of recording a radiation image therein and generating image signals according to the radiation image recorded therein; an image memory 12 that temporarily stores the image signals generated in the radiation image detector 11; a wireless communication unit 13 that outputs the image signals temporarily stored in the image memory 12 after converting to wireless communication signals; a control unit 14 that controls the operation of the radiation image detector 11, image memory 12, and wireless communication unit 13; and a substantially rectangular solid shaped case 15 that accommodates the radiation image detector 11, image memory 12, wireless communication unit 13, and control unit 14.

The radiation image detector 11 may be of any type of radiation image detector as long as it is capable of detecting radiation transmitted through a subject and outputting image signals representing the radiation image of the subject. One of such radiation image detectors, for example, is constituted by a layer structure that includes the following layers on the order listed below: a first electrode layer that transmits recording radiation; a recording photoconductive layer that shows electrical conductivity when irradiated with radiation; a charge transport layer that acts as an insulator against the latent image charges and as a conductor for the electric charges of opposite polarity to the latent image charges; a readout photoconductive layer that shows electrical conductivity when irradiated with a readout electromagnetic wave; and a second electrode layer that transmits the readout electromagnetic wave. The radiation image detector 11 described above receives recording radiation from the side of the first electrode layer to store an amount of electric charges according to the dosage of radiation irradiated on the detector in a storage section formed at the interface between the recording photoconductive layer and charge transport layer, whereby the radiation image information is recorded therein. Thereafter, the radiation image information recorded in the radiation image detector 11 is read out when scanned with spot or line light beams. The mechanism for scanning the readout light is also accommodated in the case (not shown). Further, an indirect type radiation image detector, in which electric charges obtained by photoelectrically converting luminescence emitted from a phosphor when radiation is irradiated thereon are stored in the storage section, may also be used as the radiation image detector 11 other than the direct conversion type radiation image detector described above. Still further, the so-called TFT readout type radiation image detector may also be used. A configuration may be adopted in which a storage phosphor sheet and a readout unit for irradiating excitation light on the storage phosphor sheet to read out the radiation image information using a line sensor or the like are provided in the case 15.

The wireless communication unit 13 outputs the image signals after converting to wireless communication signals as described above. Here, various existing communication protocols including UWB, Bluetooth, HiSWANa (High Speed Wireless Access Network type a), HiperLAN, Wireless 1394, Wireless USB, Wireless LAN, and the like may be used.

The control unit 14 controls the operation of the radiation image detector 11, image memory 12, and wireless communication unit 13 as described above. As shown in FIG. 1, it further includes a distance information obtaining means 14a for obtaining information that indicates a distance to the receiving unit that receives the wireless communication signals outputted therefrom; and an output control means 14b for controlling the wireless communication signals to be outputted from the wireless communication unit 13 if the distance indicated by the distance information obtained by the distance information obtaining means 14a is less than or equal to a predetermined value.

Here, the receiving unit described above is, for example, an image reproducing unit that receives the wireless communication signals outputted from the radiation image detection cassette 10, and converts the received signals to image signals to display a visible image based on the converted image signals. The image reproducing unit is constituted by a computer and a monitor. The distance information obtaining means 14a receives an output request signal through the wireless communication unit 13, and measures the distance between the receiving unit and the radiation image detection cassette 10 according to the received output request signal, the operation of which will be described in detail later. The output request signal as used herein means a signal requesting output of image signals from the radiation image detection cassette 10 to the receiving unit.

The case 15 is constituted by a top-open box type housing 15a and a lid 15b covering the top of the housing 15a.

Hereinafter, the operation of the radiation image detection cassette 10 will be described.

First, in response to a control signal from the control unit 14 of the radiation image detection cassette 10, image signals are read out from the radiation image detector 11 having a radiation image recorded therein under predetermined imaging conditions. The image signals read out from the radiation image detector 11 are outputted to the image memory 12 and temporarily stored therein. Here, a configuration may be adopted in which a signal instructing the initiation of the image signal reading described above is outputted from the receiving unit and inputted to the control unit 14 through the wireless communication unit 13, or in which an input device such as an operation panel is provided on the radiation image detection cassette 10, and the initiation of the image signal reading is instructed through the input device.

Then, an output request signal for outputting the image signals is outputted from a receiving unit, which is inputted to the distance information obtaining means 14a of the control unit 14 through the wireless communication unit 13. The distance information obtaining means 14a outputs a distance measuring wireless communication signal to the receiving unit through the communication unit 13 for measuring the distance to the receiving unit when the output request signal is received in the manner as described above. Then, the receiving unit outputs a response signal as a wireless communication signal to the radiation image detection cassette 10 immediately after receiving the distance measuring wireless communication signal. Here, it is assumed that the wireless communication signal outputted from the wireless communication unit 13 includes a signal for identifying the receiving unit, and the response signal outputted from the receiving unit includes a signal for identifying the radiation image detection cassette 10.

Then, the response signal outputted from the receiving unit is received by the wireless communication unit 13 and inputted to the distance information obtaining means 14a. The distance information obtaining means 14a measures the time period t1 from the time point when the distance measuring wireless communication signal is outputted to the receiving unit to the time point when the response signal outputted from the receiving unit is received. Then, based on the time period t1, it calculates the distance d between the radiation image detection cassette 10 and the receiving unit using the following formula. Here, it is assumed that t2 in the following formula is preset in the distance information obtaining means 14a.

$$d = c \times (t1 - t2)/2$$

where c: speed of light t2: time period from the time point when the distance measuring wireless communication signal is received by the receiving unit to the time point when the response signal is outputted from the receiving unit.

Figure 2:
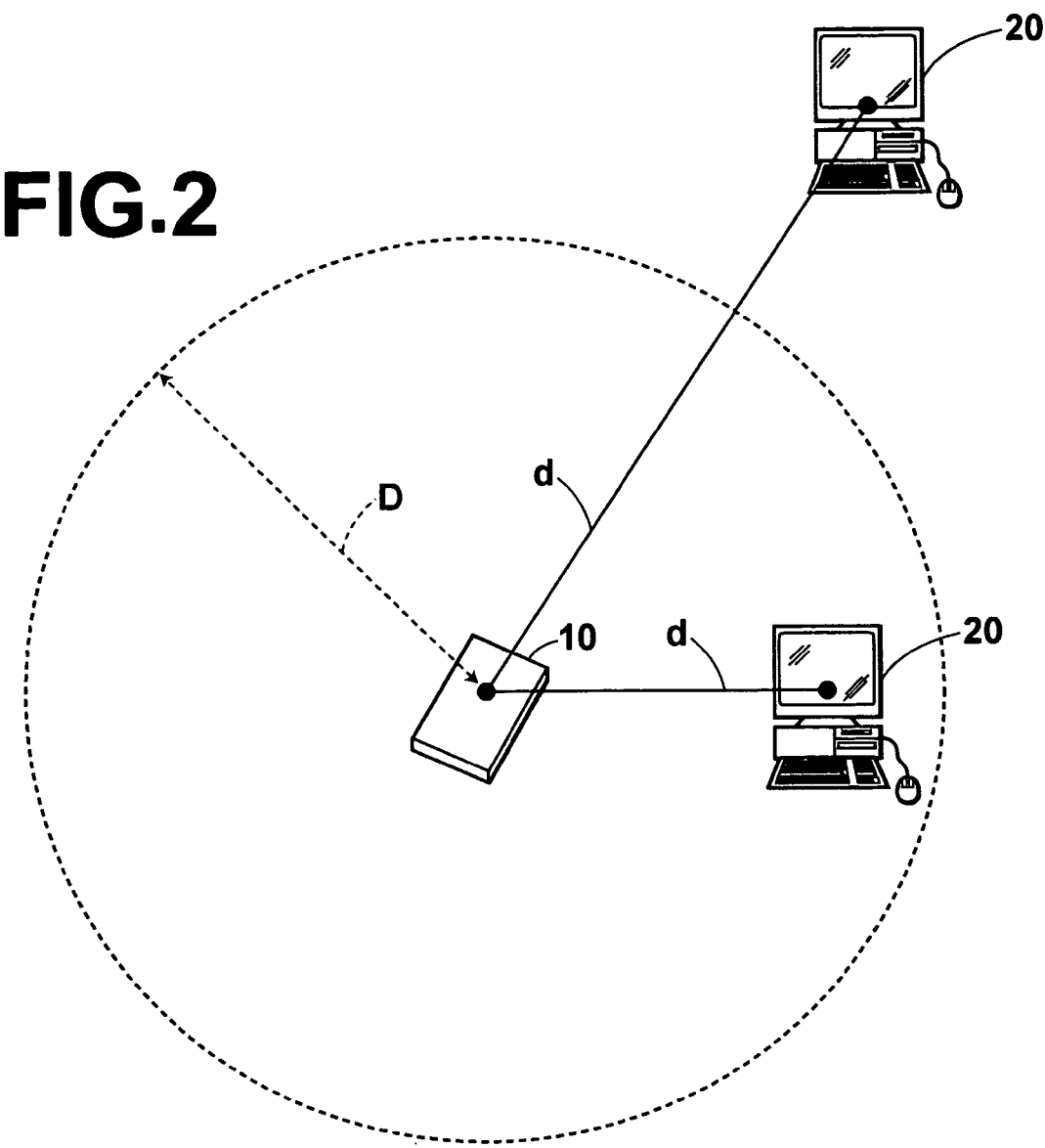
FIG. 2 is an illustrative drawing for explaining the operation of the radiation image detection cassette shown in FIG. 1.
Figure 3:
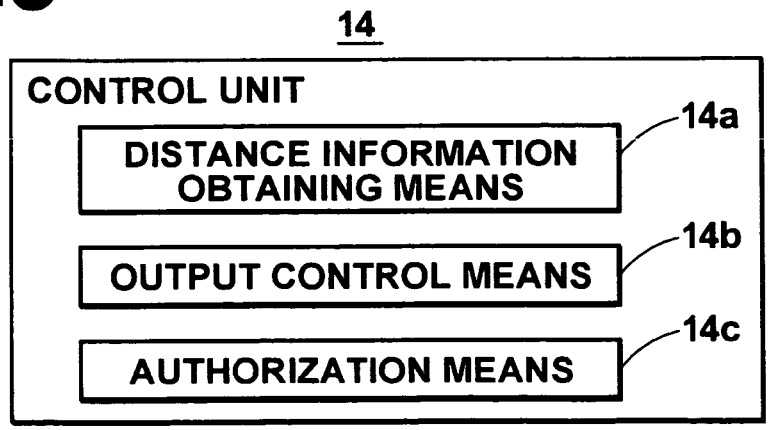
FIG. 3 is a block diagram of the control section of the radiation image signal output control apparatus according to another embodiment of the present invention, illustrating the schematic construction thereof.

The distance information obtaining means 14a outputs the distance d calculated in the manner as described above to the output control means 14b. Then, as shown in FIG. 2, if the distance d between the radiation image detection cassette 10 and the receiving unit 20 is determined to be less than or equal to a predetermined value D, that is, if the receiving unit 20 is determined to be located within the dotted line circle shown in FIG. 2, the output control means 14b reads out image signals from the image memory 12. Then, the image signals read out from the image memory 12 by the output control means 14b are converted to wireless communication signals and outputted toward the receiving unit 20 by the wireless communication unit 13. On the other hand, if the distance d between the radiation image detection cassette 10 and the receiving unit 20 is determined to be greater than the predetermined value D, that is, if the receiving unit 20 is determined to be located outside of the dotted line circle shown in FIG. 2, image signals are not read out from the image memory 12, and wireless communication signals are not outputted from the wireless communication unit 13. Here, a configuration may be adopted in which a signal is outputted from the radiation image detection cassette 10 to the receiving unit 20 through the wireless communication unit 13 indicating that the distance between the radiation image detection cassette 10 and the receiving unit 20 is too long to output the image signals when the distance d between the radiation image detection cassette 10 and the receiving unit 20 is determined to be greater than the predetermined value D.

According to the radiation image detection cassettes 10 that employs the aforementioned embodiment, distance information that indicates a distance between the radiation image detection cassette 10 and receiving unit 20 is obtained, and if the distance indicated by the distance information obtained is less than or equal to a predetermined value, wireless communication signals are controlled to be outputted from an output unit, while the distance described above is greater than the predetermined value, the wireless communication signals are controlled not to be outputted from the output unit. This arrangement may prevent the wireless communication signals from being intercepted randomly, and allows the wireless communication signals to be outputted to particular receiving units, for example, only to those provided in some of the examination rooms or in the hospital, whereby the security for preventing personal information leakage of a patient may be enhanced.

Further, in the radiation image detection cassette 10 described above, the output control means 14b is constructed to control the wireless communication signals based only on the distance between the radiation image detection cassette 10 and the receiving unit 20. But, a configuration may be adopted in which the receiving unit outputs an identification signal that identifies the receiving unit, and the control unit 14 further includes an authorization means for receiving the identification signal and authorizing the output of the wireless communication signals from the radiation image detection cassette 10 according to the contents of the identification signal, and the output control means 14b allows the output of the wireless communication signals from the radiation image detection cassette 10, when the distance d obtained by the distance information obtaining means 14a is less than or equal to the predetermined value D, and the authorization for outputting the wireless signals is given by the authorization means 14c. The identification signal as used herein means a signal that indicates, for example, a password, and the authorization means 14c authorizes the output of the wireless communication signals from the radiation image detection cassette 10 when it receives an identification signal indicating a password that corresponds to one of the preset passwords therein.

Figure 4:
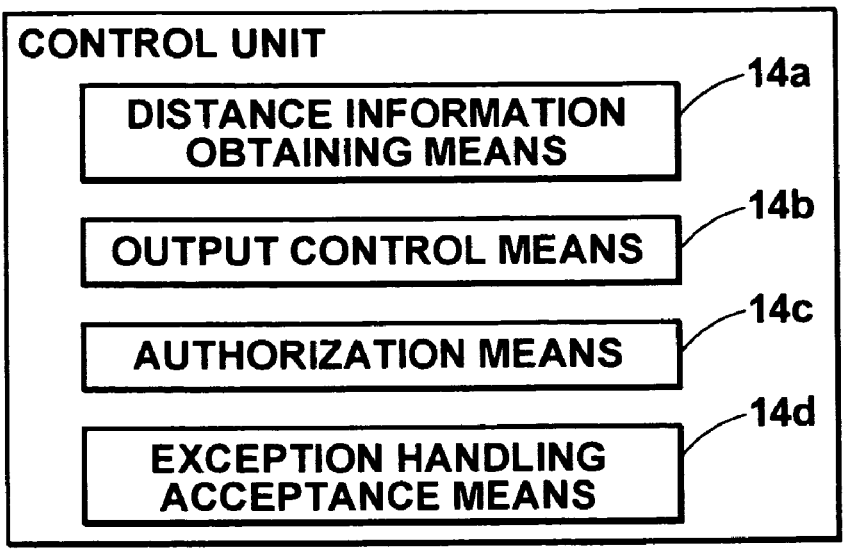
FIG. 4 is a block diagram of the control section of the radiation image signal output control apparatus according to still another embodiment of the present invention, illustrating the schematic construction thereof.

Still further, a configuration may be adopted in which the control unit further includes an exception handling acceptance means 14d that accepts an exception handling signal outputted from a receiving unit as shown in FIG. 4, and the output control means 14b allows the output of the wireless communication signals from the radiation image detection cassette 10 regardless of the distance d described above, when the exception handling signal is accepted by the exception handling acceptance means 14d. The exception handling signal as used herein means, for example, a signal used when the wireless communication signals need to be outputted from the radiation image detection cassette 10 regardless of the distance d described above, such as in an emergency situation.

Figure 5:
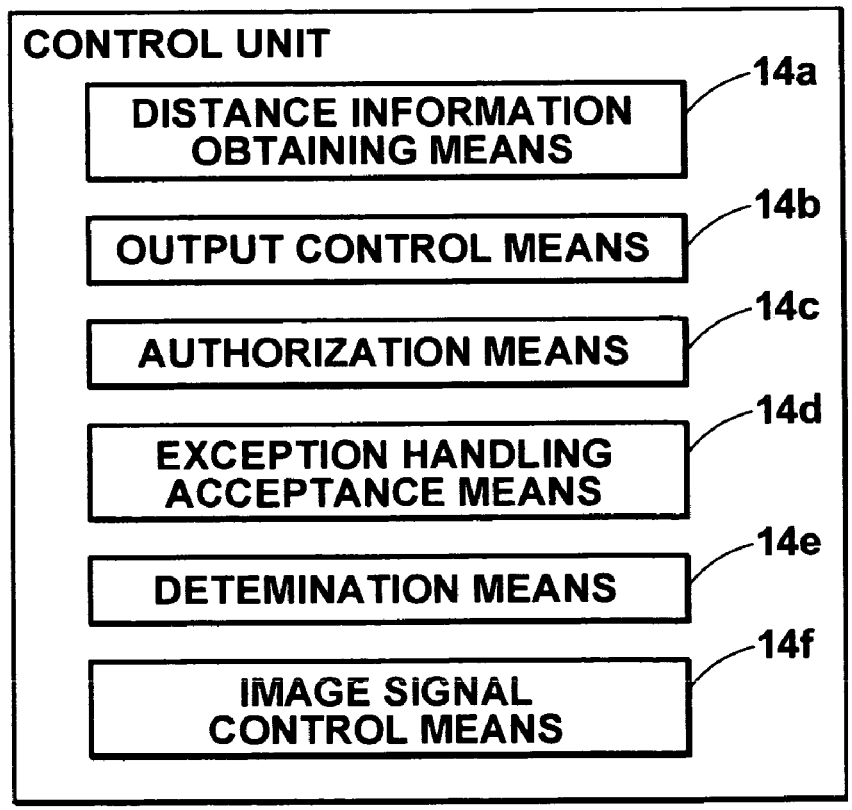
FIG. 5 is a block diagram of the control section of the radiation image signal output control apparatus according to a further embodiment of the present invention, illustrating the schematic construction thereof.

Further, the control unit 14 may further include a determination means 14e and an image signal control means 14f as shown in FIG. 5. When the image signals temporarily stored in the image memory 12 are converted to the wireless communication signals and outputted from the radiation image detection cassette 10, the determination means 14e determines if the wireless communication signals are correctly received by the receiving unit, and when the wireless communication signals are determined by the determination means 14e to have been correctly received by the receiving unit, the image signal control means 14f makes the image signals corresponding to the wireless signals correctly received by the receiving unit unreadable from the image memory 12. After the wireless communication signals are outputted from the radiation image detection cassette 10, the determination means 14e outputs a reception verification signal to the receiving unit. When the receiving unit receives the reception verification signal, it turns on a verification function to verify if the wireless communication signals are correctly received, and the image signals represented by the wireless communication signals are stored in a memory. If the image signals are correctly stored in the memory, the receiving unit outputs a reception completed signal to the radiation image detection cassette 10. If the reception completed signal is received by the radiation image detection cassette 10 within a predetermined time period, the wireless communication signals are determined by the determination means 14e to have been correctly received by the receiving unit, and if not the they are determined not to have been correctly received by the receiving unit. If the wireless communication signals are determined by the determination means 14f to have been received correctly by the receiving unit, the image signal control means 14f erases the image signals from the image memory 12. Here, the image signal control means 14f may be constructed to encrypt the image signals or overwrite the image signals stored in the image memory 12 with random data, instead of erasing from the image memory 12 as described above. That is, any process may be performed by the image signal control means 14f as long as it makes the image signals unreadable as image signals. Alternatively, a configuration may be adopted in which, when image signals are read out from the radiation image storage medium 11 and stored in the image memory 12, the image signals are encrypted by the image signal control means 14f using a predetermined encryption key before being stored in the image memory 12, and when the image signals are outputted as the wireless communication signals, the encrypted image signals are decrypted to the original image signals using the encryption key and outputted as wireless communication signals. Then, if the wireless communication signals are determined by the determination means 14e to have been correctly received by the receiving unit, the encryption key is erased. A further configuration may be adopted in which the encrypted image signals stored in the image memory 12 are converted to wireless communication signals without being decrypted and outputted to the receiving unit, together with the encryption key converted to wireless communication signal, and if the image signals and encryption key are determined by the determination means 14e to have been correctly received by the receiving unit, the encryption key on the side of the radiation image detection cassette 10 is erased.

In the embodiment described above, a configuration is adopted in which the distance measuring wireless communication signal is outputted from the radiation image detection cassette 10 in response to the output request signal from the receiving unit, and the response signal is outputted from the receiving unit to measure the distance between the radiation image detection cassette 10 and receiving unit. But the configuration is not limited to this, and a further configuration may be adopted in which, for example, the radiation image detection cassette 10 further includes a directional antenna that receives the output request signal to recognize the direction in which the receiving unit is present. Then, USB radio waves are transmitted from the radiation image detection cassette 10 to measure the distance between the image detection cassette 10 and receiving unit based on the principle of a radar. The distance measuring method is not limited to those described above, and any of the existing distance measuring methods may be used as long as it is a method that uses wireless communication signals.

Further, in the aforementioned description, a radiation image detection cassette that employs an embodiment of the radiation image signal control method and apparatus of the present invention has been described. But, the application of the present invention is not limited to the radiation image detection cassette described above, and it may be also applied to any output unit having different configuration as long as it is constructed to read out image signals from the radiation image detector 11 according to the radiation image recorded therein and output the image signals read out therefrom after converting to wireless communication signals. For example, the embodiment described above may also be applied to a radiation image readout system permanently installed at a fixed location, not only to those of the portable type like the radiation image detection cassette. Further, the receiving unit is not limited to those installed at a fixed position, and may includes, for example, a notebook computer or the like.

What is claimed is:

1. A radiation image signal output control method, comprising the steps of:
    obtaining by a processor distance information that indicates a distance between an output unit, which reads out image signals from a radiation image recording medium according to a radiation image recorded thereon and outputs the image signals read out therefrom after converting to wireless communication signals, and a receiving unit that receives the wireless communication signals outputted from the output unit;
    controlling by the processor the wireless communication signals to be outputted from the output unit if the distance indicated by the distance information obtained is less than or equal to a predetermined value, and not to be outputted therefrom if the distance is greater than the predetermined value;
    temporarily storing image signals read out from the radiation image recording medium according to the radiation image recorded thereon;
    determining if the image signals temporarily stored in the storage means and outputted from the output unit after converted to wireless communication signals are correctly received by the receiving unit; and
    making, when the wireless communication signals are determined to have been correctly received by the receiving unit, the image signals temporarily stored in the storage means corresponding to the wireless communication signals correctly received by the receiving means unreadable.

2. A radiation image signal output control apparatus, comprising:
    a distance information obtaining means for obtaining distance information that indicates a distance between an output unit, which reads out image signals from a radiation image recording medium according to a radiation image recorded thereon and outputs the image signals read out therefrom after converting to wireless communication signals, and a receiving unit that receives the wireless communication signals outputted from the output unit;
    an output control means for controlling the wireless communication signals to be outputted from the control unit if the distance indicated by the distance information obtained by the distance information obtaining means is less than or equal to a predetermined value, and not to be outputted therefrom if the distance is greater than the predetermined value;
    a storage means for temporarily storing image signals read out from the radiation image recording medium according to the radiation image recorded thereon;
    a determination means for determining if the image signals, which are temporarily stored in the storage means and outputted from the output unit after converted to wireless communication signals, are correctly received by the receiving unit; and
    an image signal control means for making, when the wireless communication signals are determined by the determination means to have been correctly received by the receiving unit, the image signals temporarily stored in the storage means corresponding to the wireless communication signals correctly received by the receiving means unreadable.

3. A radiation image signal output control apparatus as defined in claim 2, wherein:
    a distance d between the output unit and the receiving unit is calculated based on a time t1, which is an amount of time elapsed between a timing at which the distance information obtaining means outputs a distance measuring wireless communication signal and a timing at which a response signal output from the receiving unit is received, according to the following formula:

$d = c \cdot (t1 - t2)/2$ wherein c is the speed of light, and t2 is an amount of time elapsed between a timing at which the receiving unit receives the distance measuring wireless communication signal and a timing at which the receiving unit outputs the response signal.

4. A radiation image signal output control apparatus as defined in claim 2, wherein:
    the output unit outputs a signal that indicates that the wireless communication signals cannot be transmitted due to the distance between the output unit and the receiving unit being too great to the receiving unit.

5. A radiation image signal output control apparatus as defined in claim 2, wherein:
    the determination means determines that the receiving unit has correctly received the wireless communication signals in cases that an amount of time elapsed between a timing at which the wireless communication signals are output from the output unit and a timing at which a reception completion signal output by the receiving unit when the wireless communication signals are correctly received by the receiving unit is a predetermined amount of time or less.

6. A radiation image signal output control apparatus as defined in Claim 2, wherein:
    the image signal control means stores the image signals in the storage means in an encrypted state.

7. A radiation image signal output control apparatus as defined in claim 2, wherein:
    the image signal control means deletes an encryption key for decrypting the image signals stored in the storage means after the encryption key is employed to decrypt the image signals stored in the storage means, output by the output unit, and the determination means determines that the wireless communication signals have been correctly received by the receiving unit.

8. A radiation image signal output control apparatus as defined in claim 2, wherein:
    the image signal control means deletes an encryption key for decrypting the image signals stored in the storage means after the encrypted image signals in the storage means and the encryption key are output by the output unit as the wireless communication signals, and the determination means determines that the wireless communication signals have been correctly received by the receiving unit.

9. A radiation image signal output control apparatus as defined in claim 2, wherein:
    the image signal control means overwrites the image signals stored in the storage means with random data.

* * * * *